(12) United States Patent
Kishore et al.

(10) Patent No.: US 10,565,081 B2
(45) Date of Patent: Feb. 18, 2020

(54) DATA PROTECTION MANAGER

(71) Applicant: CERNER INNOVATION, INC., Kansas City, KS (US)

(72) Inventors: Buyyarapyu Pavan Kishore, Bengalūru (IN); Akkaladevi Vijay Krishna, Bengalūru (IN); Jagadish Mohith, Bengalūru (IN); Ramesh Monisha, Bengalūru (IN); Nese Manjunatha, Bengalūru (IN); Ravishankar Nagesh, Bengalūru (IN)

(73) Assignee: Cerner Innovation, Inc., Kansas City, KS (US)

( * ) Notice: Subject to any disclaimer, the term of this patent is extended or adjusted under 35 U.S.C. 154(b) by 155 days.

(21) Appl. No.: 15/856,574

(22) Filed: Dec. 28, 2017

(65) Prior Publication Data
US 2019/0205235 A1    Jul. 4, 2019

(51) Int. Cl.
| | |
|---|---|
| *G06F 11/00* | (2006.01) |
| *G06F 11/32* | (2006.01) |
| *G06F 11/14* | (2006.01) |
| *G06Q 10/06* | (2012.01) |
| *G06F 3/0483* | (2013.01) |
| *G16H 10/00* | (2018.01) |

(52) U.S. Cl.
CPC ......... *G06F 11/327* (2013.01); *G06F 3/0483* (2013.01); *G06F 11/1448* (2013.01); *G06F 11/1464* (2013.01); *G06Q 10/063* (2013.01); *G16H 10/00* (2018.01)

(58) Field of Classification Search
CPC .............. G06F 11/327; G06F 11/1464; G06F 11/1448; G06F 3/0483; G06Q 10/063; G16H 10/00
USPC ........................................................ 714/57
See application file for complete search history.

(56) References Cited

U.S. PATENT DOCUMENTS

| | | | |
|---|---|---|---|
| 7,664,797 B1 * | 2/2010 | Weisgerber | G06F 11/1464 714/6.12 |
| 8,959,056 B1 * | 2/2015 | Weisgerber | H04L 67/06 707/653 |
| 10,430,293 B1 * | 10/2019 | Skowronski | G06F 11/1469 |

* cited by examiner

*Primary Examiner* — Yair Leibovich
(74) *Attorney, Agent, or Firm* — Shook, Hardy & Bacon LLP

(57) ABSTRACT

Systems, methods, and computer-readable media for data protection management are provided. Failure notifications corresponding to backup failures of client servers in a healthcare facility are received and a dashboard associated with the backup failures is provided. The dashboard comprises user information that identifies users assigned to each backup failure. In embodiments, the dashboard enables a user to update a status of a backup failure and add, access, and modify records corresponding to a backup failure. In some embodiments, the dashboard is integrated with a service management application that enables the user to create a service request from the dashboard. A report corresponding to the dashboard is generated and communicated to a leadership team. The report includes statistics corresponding to backup failures addressed by each associate and backup failures identified per region or unit of a healthcare facility.

20 Claims, 6 Drawing Sheets

| Region | Total No. of Client Servers Backups failing for the following No. of days | | | | | | | Total |
|---|---|---|---|---|---|---|---|---|
| | 1 | 2 | 3 | 4 | 5 | 6 | 7 | |
| Central | 0 | 0 | 0 | 1 | 1 | 1 | 1 | 4 |
| CTS CSM | 1 | 0 | 0 | 0 | 0 | 1 | 3 | 5 |
| eHosting | 1 | 0 | 0 | 0 | 0 | 0 | 0 | 1 |
| ETS | 5 | 0 | 2 | 0 | 0 | 1 | 0 | 8 |
| Federal | 1 | 2 | 0 | 0 | 0 | 1 | 0 | 4 |
| Midwest | 0 | 0 | 0 | 1 | 1 | 0 | 2 | 4 |
| North Atlantic | 0 | 0 | 0 | 1 | 0 | 0 | 3 | 4 |
| Other | 0 | 1 | 1 | 1 | 3 | 1 | 9 | 16 |
| Southeast | 3 | 1 | 1 | 0 | 0 | 1 | 6 | 12 |
| West | 0 | 0 | 0 | 0 | 0 | 0 | 2 | 2 |
| Total | 11 | 4 | 4 | 4 | 5 | 6 | 26 | 60 |

FIG. 6

DATA PROTECTION MANAGER

BACKGROUND

Disaster recovery systems are critical to healthcare data. Daily, or more frequent, backups help maintain the integrity of the healthcare data. Unfortunately, various circumstances cause a number of daily backups to fail. In a healthcare setting, the number of client servers subject to daily backups is often in the thousands. Accordingly, the number of failures may be troubling high. In an effort to combat these failures, data protection teams proactively monitor and resolve any daily backup failures. To do so, requires manually tracking the backups in a spreadsheet. If a spreadsheet is shared among several people, data inconsistencies can result if updates to the data are not committed at regular intervals. Additionally, reporting monthly or quarterly statistics to the leadership requires a significant amount of manual effort to consolidate multiple spreadsheets. Moreover, the work that is required lacks visibility at the leadership level and the overall efforts and contributions made by the data protection team to protect client data.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to methods, systems, and computer readable media for providing data protection management. Failure notifications corresponding to backup failures of client servers in a healthcare facility are received and a dashboard associated with the backup failures is provided. The dashboard comprises user information that identifies users assigned to each backup failure. In embodiments, the dashboard enables a user to update a status of a backup failure and add, access, and modify records corresponding to a backup failure. In some embodiments, the dashboard is integrated with a service management application that enables the user to create a service request from the dashboard. A report corresponding to the dashboard is generated and communicated to a leadership team. The report includes statistics corresponding to backup failures addressed by each associate and backup failures identified per region or unit of a healthcare facility.

BRIEF DESCRIPTION OF THE DRAWINGS

Embodiments are described in detail below with reference to the attached drawing figures, wherein:

FIGS. 5-6 are illustrative screen displays in accordance with embodiments of the present invention.

DETAILED DESCRIPTION

Figure 1:
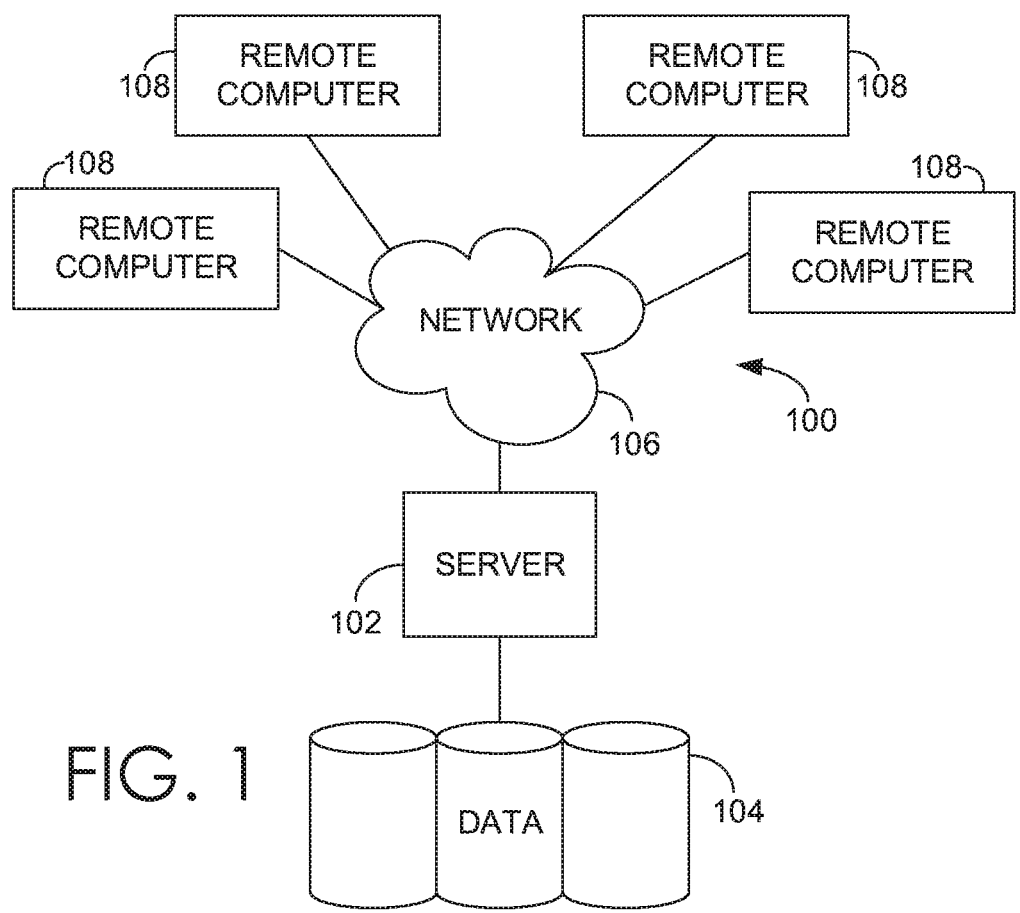
FIG. 1 is a block diagram of an exemplary computing environment suitable for use in implementing embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

As noted in the Background, disaster recovery systems are critical to healthcare data. Daily, or more frequent, backups help maintain the integrity of the healthcare data. Unfortunately, various circumstances cause a number of daily backups to fail. In a healthcare setting, the number of client servers subject to daily backups is often in the thousands. Accordingly, the number of failures may be troubling high. In an effort to combat these failures, data protection teams proactively monitor and resolve any daily backup failures. To do so, requires manually tracking the backups in a spreadsheet. If a spreadsheet is shared among several people, data inconsistencies can result if updates to the data are not committed at regular intervals. Additionally, reporting monthly or quarterly statistics to the leadership requires a significant amount of manual effort to consolidate multiple spreadsheets. Moreover, the work that is required lacks visibility at the leadership level and the overall efforts and contributions made by the data protection team to protect client data.

Embodiments of the present disclosure relate to systems and methods for providing data protection management. Failure notifications corresponding to backup failures of client servers in a healthcare facility are received and a dashboard associated with the backup failures is provided. The dashboard comprises user information that identifies users assigned to each backup failure. In embodiments, the dashboard enables a user to update a status of a backup failure and add, access, and modify records corresponding to a backup failure. In some embodiments, the dashboard is integrated with a service management application that enables the user to create a service request from the dashboard. A report corresponding to the dashboard is generated and communicated to a leadership team. The report includes statistics corresponding to backup failures addressed by each associate and backup failures identified per region or unit of a healthcare facility.

Accordingly, one embodiment of the present disclosure is directed to a system for providing a data protection manager. The system includes a processor; and a computer storage medium storing computer-usable instructions that, when used by the processor, cause the processor to: receive failure notifications corresponding to backup failures of client servers in a healthcare facility; provide a dashboard associated with the backup failures, the dashboard comprising user information that identifies the user assigned to each backup failure; and generate a report corresponding to the dashboard, the report being communicated to a leadership team and including statistics corresponding to backup failures addressed by each associate and backup failures identified per region or unit of a healthcare facility.

In another embodiment, the present disclosure directed to a computerized method for providing a data protection manager. The method receiving failure notifications corresponding to backup failures of client servers in a healthcare facility. The method also includes providing a dashboard associated with the backup failures, the dashboard comprising user information that identifies the user assigned to each backup failure. The method further includes generating a report corresponding to the dashboard, the report being communicated to a leadership team and including statistics corresponding to backup failures addressed by each associate and backup failures identified per region or unit of a healthcare facility.

In yet another embodiment, the present disclosure is directed to one or more computer storage media having computer-executable instructions embodied thereon that, when executed by a computer, causes the computer to perform operations to provide a data protection manager. The operations include receiving failure notifications corresponding to backup failures of client servers in a healthcare facility. The operations also include providing a dashboard associated with the backup failures, the dashboard comprising user information that identifies the user assigned to each backup failure. The operations further include generating a report corresponding to the dashboard, the report being communicated to a leadership team and including statistics corresponding to backup failures addressed by each associate and backup failures identified per region or unit of a healthcare facility.

Having briefly described embodiments of the present invention, an exemplary operating environment suitable for use in implementing embodiments of the present invention is described below. FIG. 1 provides an aspect of an example operating environment with which embodiments of the present invention may be implemented. The aspect of an operating environment is illustrated and designated generally as reference numeral 100.

Example operating environment 100 comprises a general purpose computing device in the form of a control server 102. Exemplary components of the control server 102 comprise a processing unit, internal system memory, and a suitable system bus for coupling various system components, including database cluster 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Control server 102 typically includes therein, or has access to, a variety of computer-readable media, for instance, database cluster 104. Computer-readable media can be any available media that might be accessed by control server 102, and includes volatile and nonvolatile media, as well as, removable and nonremovable media. Computer-readable media might include computer storage media. Computer storage media includes volatile and nonvolatile media, as well as removable and nonremovable media implemented in any method or technology for storage of information, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or any other magnetic storage device, or any other medium which can be used to store the desired information and which may be accessed by the control server 102. Computer storage media does not comprise signals per se. Combinations of any of the above also may be included within the scope of computer-readable media.

The computer storage media discussed above and illustrated in FIG. 1, including database cluster 104, provide storage of computer-readable instructions, data structures, program modules, and other data for the control server 102. In some embodiments, data cluster 104 takes the form of a cloud-based data store, and in some embodiments is accessible by a cloud-based computing platform.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and providers' offices. Providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like.

The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

In some embodiments, remote computers 108 comprise computing-devices that are part of a cloud-computing platform. For example, the control server 102 might operate in a computer network 106 hosted as part of a cloud service (e.g., AMAZON WEB SERVICES, GOOGLE HOSTING, IBM BLUEMIX). In some embodiments, a remote computer 108 is associated with a health records data source such as an electronic health record (EHR) system of a hospital or medical organization, a health information exchange EHR, insurance provider EHR, ambulatory clinic EHR, or patient-sensor, or other data source, and facilitates accessing data of the source and communicating the data to control server 102 and/or other computing devices on a cloud computing platform, including other remote computers 108.

Exemplary computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networked environment, program modules or portions thereof might be stored in association with the control server 102, the database cluster 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

In some embodiments, control server 102 is a computing system or platform made up of one or more computing devices. Embodiments of control server 102 may be a distributed computing system, a centralized computing system, a single computer such as a desktop or laptop computer or a networked computing system. Thus, in some embodiments, control server 102 comprises a multi-agent computer system with software agents.

Figure 2:
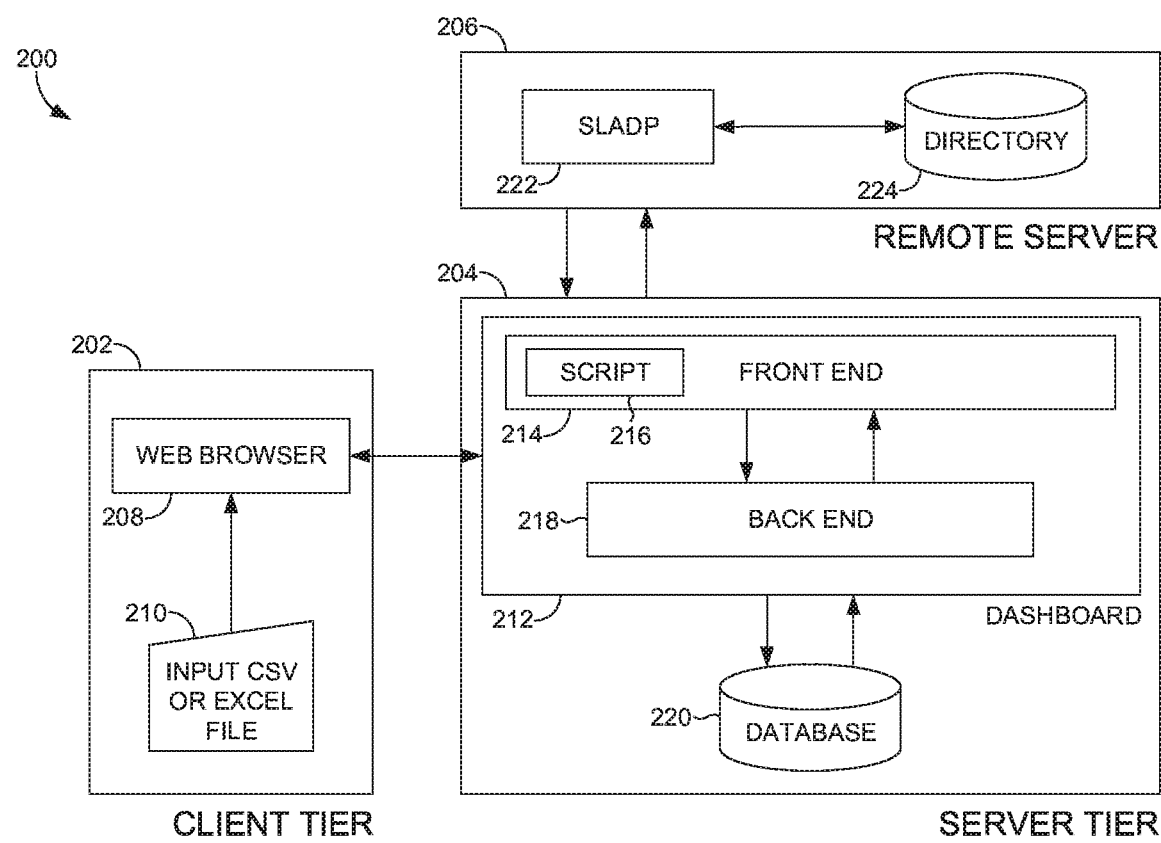
FIG. 2 is an exemplary system architecture suitable for use in implementing embodiments of the present invention.

Turning now to FIG. 2, an exemplary framework of a data protection system 200 is shown, in accordance with an aspect of the present invention. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory. The data protection system 200 may be implemented via any type of computing device, such as computing device 100 described above with reference to FIG. 1, for example.

The data protection system 200 generally operates to provide a data protection manager. The data protection manager manages backup failures and stores information corresponding to the backup failures (e.g., assigned users, progress updates, etc.). Accordingly, reports can be generated and communicated to the backup team and leadership on a scheduled basis.

The data protection manager provides a dashboard that is a one-stop solution for maintaining and managing backup failures. The dashboard provides in-depth understanding of backup failures that can assist backup administrators to address the pressing issues immediately. The dashboard proactively tracks the backup failures, tasks, and updates and obviates the need of individual users to maintain records of assigned backup failures, tasks, and updates. The dashboard consists of a user friendly graphical interface which allows a user to add, access, and modify records. Data from the dashboard can be provided to the users in the form of a table that allows an individual user to assign the user to a task and specify progress in the form of status changes. The dashboard can prevent two or more users from being assigned to the same task or from trying to fix the same problem.

In embodiments, the dashboard provides an in-depth summary of backup failures each day (or configurable period of time). Additionally, the dashboard can provide statistics on the number of failures fixed by each user and a number of failures that occur in each region (or business unit, location, or a configurable arrangement of client servers). Repetitive failures can be highlighted by the dashboard (or marked in a particular color, font, etc.) to draw attention to backup administrators. Similarly, repetitive failures can be distinguished from each other based on a duration of the failures (e.g., failures that have failed for three days may appear in one color, while failures that have failed for five days may appear in another color).

In embodiments, the dashboard is integrated with Lightweight Directory Access Protocol (LDAP) so authentication can be provided on a remote server in a secure location. This enables the dashboard to be restricted to only users from the organization. Additionally, LDAP may contain SLDAP, which is an intermediator between the application and the remote directory, to facilitate the validation of information.

Additionally, or alternatively, the dashboard may be integrated with a service management application. The service management application integration may enable a user to create a service request from the dashboard, thus obviating the need to assign tasks to a user from the service management application.

In practice, and referring back to FIG. 2, a user of the data protection system 200 may initially access the dashboard from a web browser 208 on the client tier 202. A list of backup failures may be provided, for example, from the server tier 204. The list may be communicated as a CSV or EXCEL file 210. Additionally, or alternatively, the CSV or EXCEL file 210 may be input at the client tier 202 via the web browser 208.

The server tier 204 authenticates the user via a directory 224 (e.g., LDAP) and database 220 ensures that the user has permission to view the dashboard 212 in a read or write mode. The authentication may be performed by the back end process 218 of the dashboard. Additionally, the back end process 218 may also receive a list of the backup failures from the client tier 202. To facilitate the validation of information between the client tier 202 and the server tier, script 216 may be utilized.

Additionally, or alternatively, script 216 running on the front end of the dashboard 214 provides the interface that enables the user to interact with the dashboard 214. As mentioned, the dashboard provides a one-stop solution for maintaining and managing backup failures.

Figure 3:
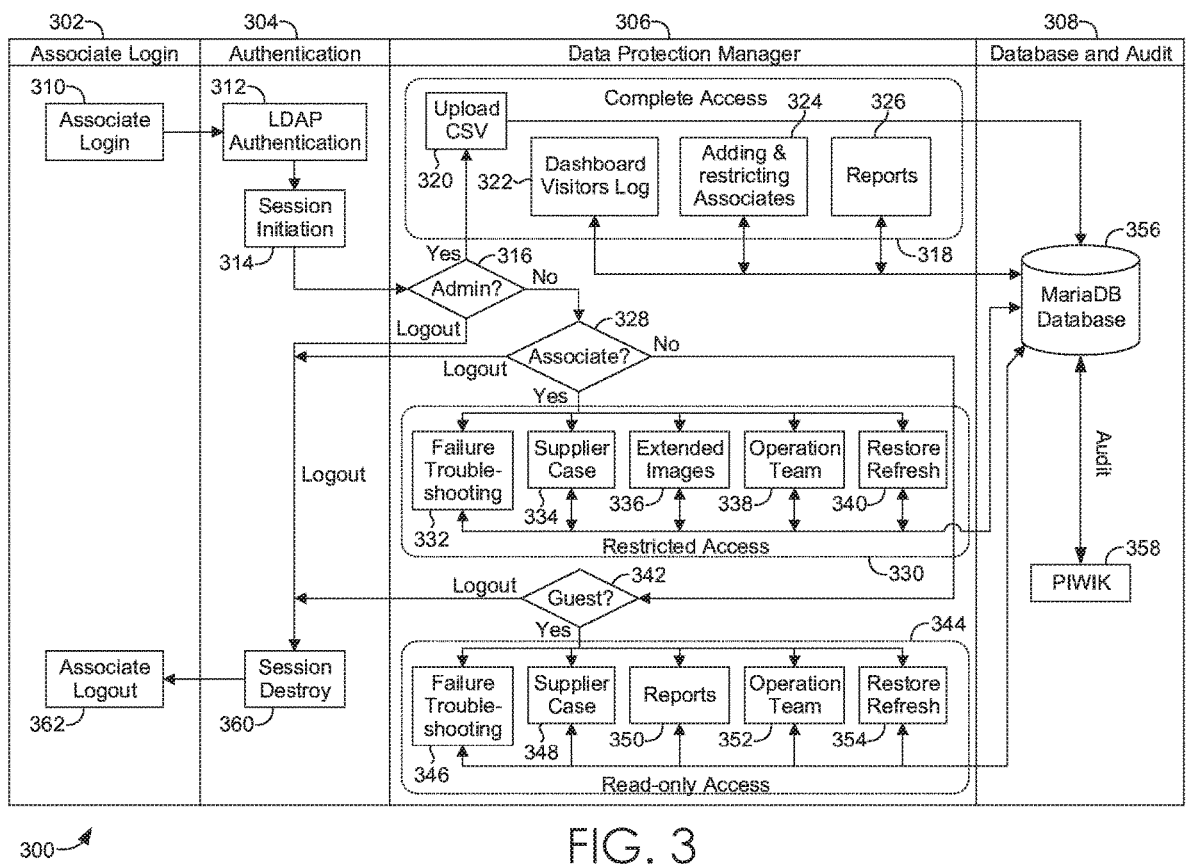
FIG. 3 is an exemplary system architecture suitable for use in implementing embodiments of the present invention.

Referring now to FIG. 3, an exemplary flow diagram is provided illustrating a method 300 for providing a data protection manager, in accordance with an embodiment of the present invention. The method may be performed by any computing device (such as computing device described with respect to FIG. 1) with access to a data protection system (such as the one described with respect to FIG. 2) or by one or more components of the data protection system 200.

Initially, at an associate login layer 302, a user (e.g., associate) logs in, at step 310, to the data protection manager layer 306. At the authentication layer 304, LDAP authentication is provided, at step 312. If successfully authenticate, a session is initiated with the data protection manager 306, at step 314. Credentials corresponding to the user are further checked at steps 316 and 328 to determine if the user is an administrator or an associate.

If the user is an administrator, they may have complete administrative access (providing access to the features of 318) to the data protection manager 306. This may enable the administrator to upload a CSV (i.e., a list of backup failures), at step 320. The administrator may also be able to view a visitors log, at step 322, add or restrict associates, at step 324, or generate reports, at step 326. When the administrator uploads a CSV, such as at step 320, the database 356 within the database and audit layer 308 is updated. Each action taken by the administrator may additionally communicate updates to the database 356, such that any user viewing the dashboard receives updates in real-time.

If on the other hand the user is an associate, as shown at step 328, the user may have restricted access (providing access to the features of 330) to the data protection manager 306. This may enable the associate to troubleshoot failures, at step 332, open a trouble ticket with a supplier (e.g., the backup software support team, other support teams for software corresponding to the particular system that is experiencing backup failures), at step 334, track backup images extended beyond an actual retention period (e.g., the data protection team may receive requests to extend the retention of backup images beyond the standard retention period to retain them for recovery purposes), at step 336, communicate with an operations team 338 for outstanding issues (e.g., storage provision, hardware replacements), or to track database backups or restores or refresh the dashboard, at step 340.

In some embodiments, the user may not be an administrator or an associate. Rather, the user may have read-only access (providing access to the features of 344) to the data protection manager 306. This may enable the guest or guest associate to view the status of troubleshoot failures, at step 346, view a trouble ticket with a supplier (e.g., the backup software support team, other support teams for software corresponding to the particular system that is experiencing backup failures), at step 348, view reports, at step 350, view communications with operations team 338, or view a backup (or restore) or refresh the dashboard, at step 354.

Once the administrator, associate, or guest logs out of the data protection manager, the session is destroyed by the authentication layer 304, at step 360. Accordingly, the user is logged out by the associate login layer 302, at step 362.

Figure 4:
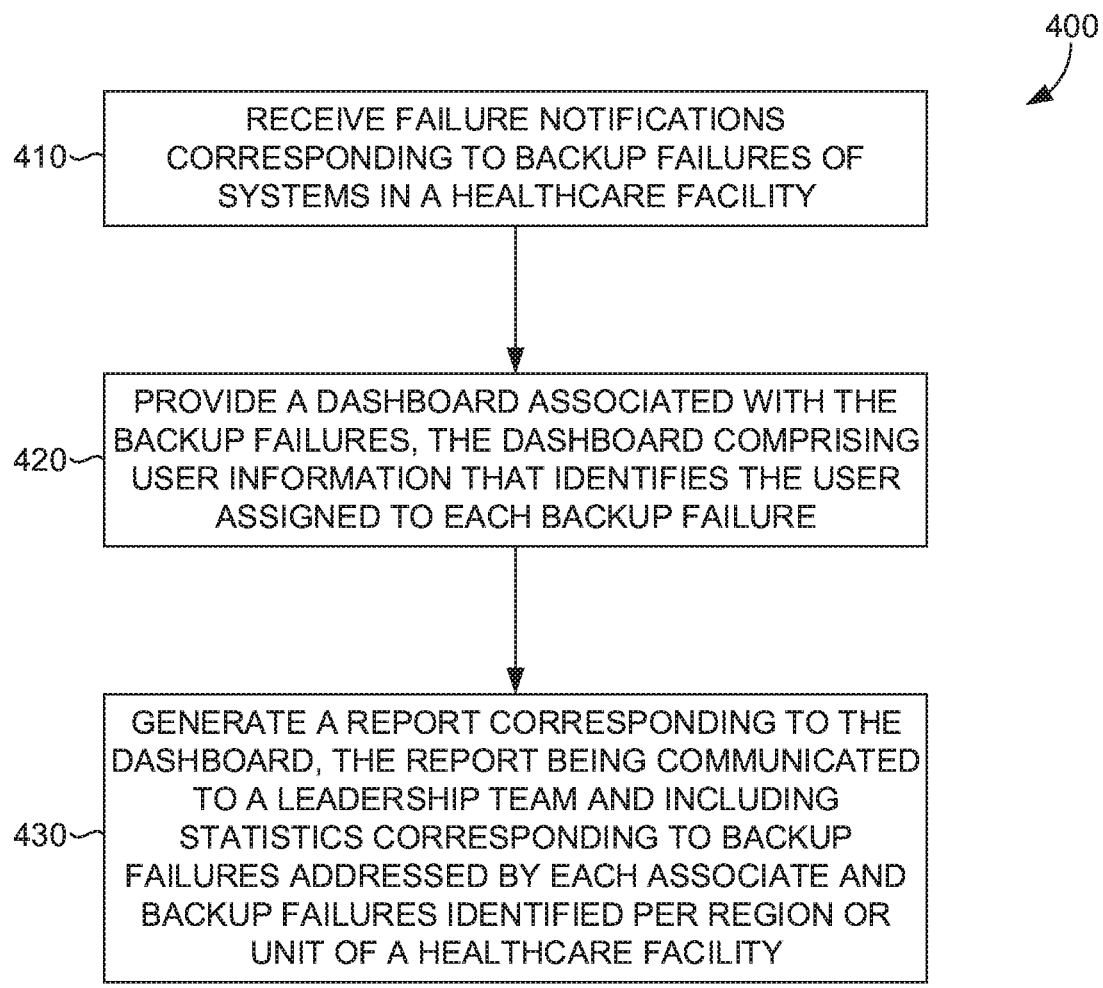
FIG. 4 is a flow diagram of a method in accordance with an embodiment of the present invention.

Turning now to FIG. 4, a flow diagram is provided illustrating a method 400 for for providing a data protection manager, in accordance with embodiments of the present invention. Method 400 may be performed by any computing device (such as computing device described with respect to FIG. 1) with access to a data protection system (such as the one described with respect to FIG. 2) or by one or more components of the data protection system 200.

Initially, at step 410, failure notifications corresponding to backup failures of client servers in a healthcare facility are received.

At step 420, a dashboard associated with the backup failures is provided. The dashboard comprises user information that identifies the user assigned to each backup failure. In some embodiments, the dashboard includes an in-depth summary of the backup failures over a time period. In some embodiments, the dashboard enables the user to update a status of a backup failure. In some embodiments, the dashboard enables the user to add, access, and modify records corresponding to a backup failure. In some embodiments, the dashboard distinguishes backup failures that have repeated a configurable number of times.

In some embodiments, the dashboard is integrated with Lightweight Directory Access Protocol. In some embodiments, the dashboard is integrated with a service management application that enables the user to create a service request from the dashboard.

At step 430, a report corresponding to the dashboard is generated. The report is communicated to a leadership team and includes statistics corresponding to backup failures addressed by each associate and backup failures identified per region or unit of a healthcare facility.

Figure 5:
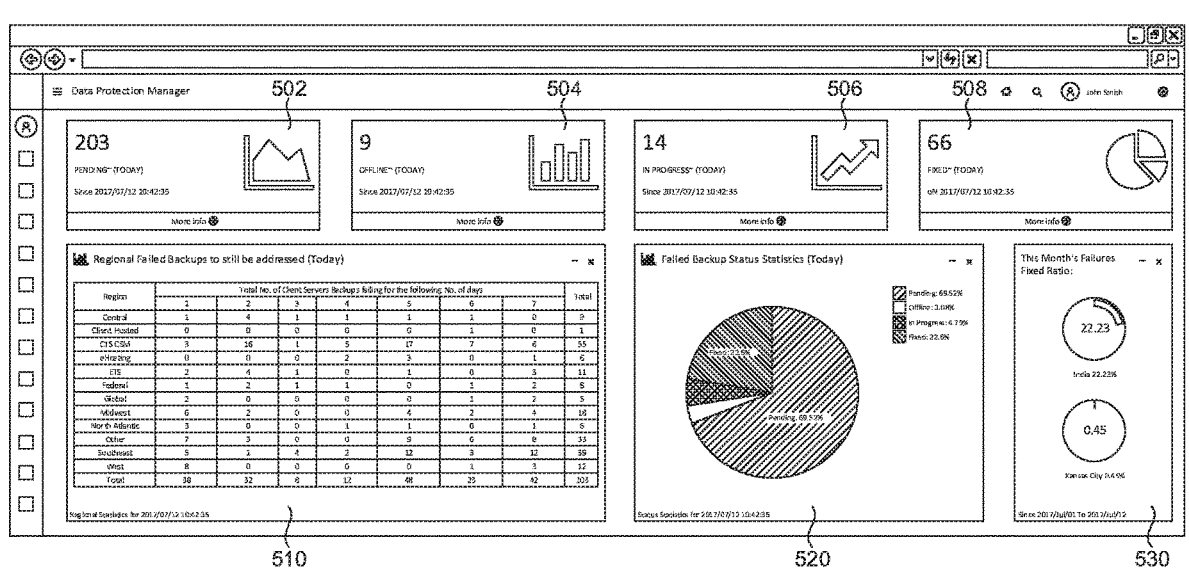

In FIGS. 5-6, illustrative screen displays are provided, in accordance with embodiments of the present invention. FIG. 5 illustrates an exemplary dashboard 500. As illustrated, a list of failed backups 510 waiting to be addressed is provided (separated by region), a chart 520 showing the percentage of pending, offline, in progress, and fixed backup failures (for the current day), a chart 530 showing the ratio of failures to fixes (for the current month for two different regions), and numerical representations 502, 504, 506, 508 for pending, offline, in progress, and fixed backup failures. Each of the numerical representations 502, 504, 506, 508 may be selected to provide more information, such as a detailed list of each client having a backup failure. For example, and referring now to FIG. 6, the numerical representation 502 for pending backup failures has been categorized into a list 600 depicting repetitive backup failures for a selected region. As illustrated, a distinction is made between backups failing for at least three days 610 and backups failing for at least five days 620. As mentioned previously, the distinction can be made based on a color, a font, a type of shading, and the like.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

The invention claimed is:

1. A system for utilizing frictionless processing auto-adjudication of medical encounters, the system comprising:
   a processor; and
   a computer storage medium storing computer-usable instructions that, when used by the processor, cause the processor to:
   receive failure notifications corresponding to backup failures of client servers in a healthcare facility;
   provide a dashboard associated with the backup failures, the dashboard comprising user information that identifies a user assigned to each backup failure;
   generate a report corresponding to the dashboard, the report being communicated to a leadership team and including statistics corresponding to backup failures addressed by a respective associate and backup failures identified per region or unit of a healthcare facility; and
   wherein the report on the dashboard presents in real time, a list of failed backups waiting to be addressed, separated by region, and a chart showing a percentage of pending, offline, in progress, and fixed backup failures for a current day.

2. The system of claim 1, wherein the dashboard includes an in-depth summary of the backup failures over a time period.

3. The system of claim 1, further comprising enabling the user to update a status of a backup failure.

4. The system of claim 1, further comprising enabling the user to add, access, and modify records corresponding to a backup failure.

5. The system of claim 1, wherein the dashboard distinguishes backup failures that have repeated a configurable number of times.

6. The system of claim 1, wherein the dashboard is integrated with Lightweight Directory Access Protocol.

7. The system of claim 1, wherein the dashboard is integrated with a service management application that enables the user to create a service request from the dashboard.

8. A computerized method for providing a data protection manager, the method comprising:
- receiving failure notifications corresponding to backup failures of client servers in a healthcare facility;
- providing a dashboard associated with the backup failures, the dashboard comprising user information that identifies a user assigned to each backup failure;
- generating a report corresponding to the dashboard, the report being communicated to a leadership team and including statistics corresponding to backup failures addressed by a respective associate and backup failures identified per region or unit of a healthcare facility; and
- wherein the report on the dashboard presents in real time, a list of failed backups waiting to be addressed, separated by region, and a chart showing a percentage of pending, offline, in progress, and fixed backup failures for a current day.

9. The method of claim 8, wherein the dashboard includes an in-depth summary of the backup failures over a time period.

10. The method of claim 8, further comprising enabling the user to update a status of a backup failure.

11. The method of claim 8, further comprising enabling the user to add, access, and modify records corresponding to a backup failure.

12. The method of claim 8, wherein the dashboard distinguishes backup failures that have repeated a configurable number of times.

13. The method of claim 8, wherein the dashboard is integrated with a Lightweight Directory Access Protocol and a service management application, the service management application enabling the user to create a service request from the dashboard.

14. One or more computer storage media having computer-executable instructions embodied thereon that, when executed by a computer, causes the computer to perform operations to provide a data protection manager, the operations comprising:
- receiving failure notifications corresponding to backup failures of client servers in a healthcare facility;
- providing a dashboard associated with the backup failures, the dashboard comprising user information that identifies the user assigned to each backup failure;
- generating a report corresponding to the dashboard, the report being communicated to a leadership team and including statistics corresponding to backup failures addressed by a respective associate and backup failures identified per region or unit of a healthcare facility; and
- wherein the report on the dashboard presents in real time, a list of failed backups waiting to be addressed, separated by region, and a chart showing a percentage of pending, offline, in progress, and fixed backup failures for a current day.

15. The media of claim 14, wherein the dashboard comprises an in-depth summary of the backup failures over a time period.

16. The media of claim 14, further comprising enabling the user to update a status of a backup failure.

17. The media of claim 14, further comprising enabling the user to add, access, and modify records corresponding to a backup failure.

18. The media of claim 14, wherein the dashboard distinguishes backup failures that have repeated a configurable number of times.

19. The media of claim 14, wherein the dashboard is integrated with Lightweight Directory Access Protocol.

20. The media of claim 14, wherein the dashboard is integrated with a service management application that enables the user to create a service request from the dashboard.

* * * * *